United States Patent [19]

Kidwell et al.

[11] 4,125,567
[45] Nov. 14, 1978

[54] TERMINAL OLEFIN PREPARATION

[75] Inventors: Roger L. Kidwell, Des Peres; Gary J. Lynch, St. Louis, both of Mo.

[73] Assignee: Monsanto Company, St. Louis, Mo.

[21] Appl. No.: 890,436

[22] Filed: Mar. 27, 1978

Related U.S. Application Data

[63] Continuation-in-part of Ser. No. 812,545, Jul. 5, 1977, abandoned.

[51] Int. Cl.² ............................ C07C 11/02; C07C 5/22
[52] U.S. Cl. ................................ 260/677 R; 260/683.2
[58] Field of Search .......................... 260/677 R, 683.2

[56] References Cited

U.S. PATENT DOCUMENTS

3,173,967  3/1965  Brown ................................ 260/683.2

OTHER PUBLICATIONS

Schwartz et al., Agnew Chem. Int. Ed. Engl.; 15, No. 6, pp. 333–340, (1976).

*Primary Examiner*—C. Davis
*Attorney, Agent, or Firm*—S. M. Tarter; E. P. Grattan; F. D. Shearin

[57] ABSTRACT

Terminal olefin is prepared by bringing together (1) a compound having the formula

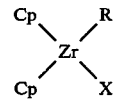

wherein Cp is a π-cyclopentadienyl radical, R is terminal alkyl and X is an essentially non-interfering monovalent entity, and (2) a mono-olefin having a carbon skeleton different from that of R under reaction conditions to displace R from (1) by (2). This process is especially useful in isomerization of internal olefins to the corresponding terminal olefins.

27 Claims, No Drawings

TERMINAL OLEFIN PREPARATION

CROSS REFERENCE TO RELATED APPLICATIONS

This application is a continuation-in-part of Application Ser. No. 812,545 filed July 5, 1977 and now abandoned.

BACKGROUND OF THE INVENTION

The economic incentives for conversion of internal olefins to terminal olefins (i.e., α-olefins or 1-olefins) are well known, and many attempts have been made to develop an attractive process for effecting such conversion. Probably the best known of the processes previously developed is that described in U.S. Pat. No. 3,173,967 issued Mar. 16, 1965 to H. C. Brown. That process comprises reacting an internal mono-olefin with an aliphatic or alicyclic hydrocarbon boron compound having at least one boron to carbon linkage, e.g., trihexylboron, trioctylboron, or diethyl diborane. As is known, however, that process is characterized by a relatively low selectivity to the desired terminal olefin and by a slow reaction rate, normally requiring temperatures as high as 160° to 180° C. for commercial utility. Stability of the boron compound is another significant drawback of that process.

More recently, it has been discovered that internal olefins can be converted to the corresponding terminal olefins by reacting an internal olefin with a zirconium chlorohydride having the formula

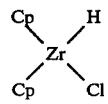

wherein Cp is an unsubstituted π-cyclopentadienyl radical and then cleaving the resulting alkylzirconium complex with trityl chloride or tetrafluoroborate in methylene chloride or benzene to provide the corresponding terminal olefin via β-hydride abstraction. A description of that procedure has been published by J. Schwartz and J. A. Labinger in ANGEW. CHEM. INT. ED. ENGL. at 15, No. 6, 333-40 (1976).

It is apparent that production of a terminal olefin from such an alkyl zirconium complex would be more attractive if it could be accomplished in a single step without the use of a costly β-hydride abstraction reagent. In the just-mentioned publication by Schwartz and Labinger, however, it is said that their attempts at such a more attractive process were not successful, and that an isomerized olefin cannot be freed from such an alkylzirconium complex by treatment with ethylene (even at high temperature and pressure) or by donor ligands such as pyridine or alkylphosphanes.

Hence, it is clear that there is a need in the art for a process in which the alkyl group can be simply and inexpensively displaced as the corresponding terminal olefin from such an alkylzirconium complex.

SUMMARY OF THE INVENTION

This invention provides a process which comprises bringing together (1) a compound having the formula

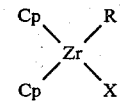

wherein each Cp is a π-cyclopentadienyl radical, R is terminal alkyl and X is an essentially non-interfering monovalent entity and (2) mono-olefin having a carbon skeleton different from that of R under reaction conditions to displace R from (1) with (2).

The reaction of this process embodiment may be illustrated as follows:

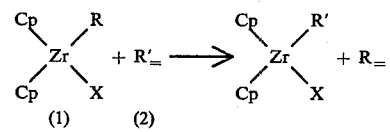

wherein Cp, R and X have their aforedescribed significance, $R_='$ is mono-olefin having a carbon skeleton different from that of R, R' is terminal alkyl having the same carbon skeleton as $R_='$, and $R_=$ is terminal olefin having the same carbon skeleton as R. In typical embodiments, the invention further comprises recovering from that mixture a terminal olefin ($R_=$) having the same carbon skeleton as R and/or a compound having the formula

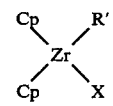

wherein Cp and X have their aforedescribed significance and R' is terminal alkyl having the same carbon skeleton as (2). In another embodiment of the invention, the above compound and a second mono-olefin are subjected to reaction conditions under which R' is displaced from that compound by said second mono-olefin, forming terminal olefin having the same carbon skeleton as (2). Thus, for use in isomerizing an internal olefin to a terminal olefin, the invention provides a process which comprises the following two steps:

(A) subjecting (1) a compound having the formula

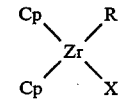

wherein Cp, R and X have their aforedescribed significance and (2) internal mono-olefin having a carbon skeleton different from that of R to reaction conditions under which R is displaced from (1) by (2) forming (3) a compound having the formula

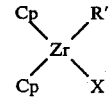

wherein Cp and X have their aforedescribed significance and R' is terminal alkyl having the same carbon skeleton as (2), and (B) subjecting a mixture of (3) and (4) mono-olefin having a carbon skeleton different from that of R' to reaction conditions under which R' is displaced from (3) by (4) forming terminal olefin having the same carbon skeleton as (2).

The reactions of this two-step process embodiment may be illustrated as follows:

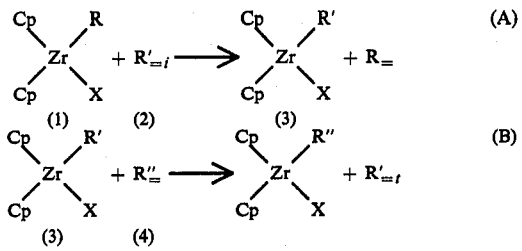

wherein Cp, R, X and $R_=$ have their aforedescribed significance, $R_{=i}'$ is internal mono-olefin having a carbon skeleton different from that of R, R' is terminal alkyl having the same carbon skeleton as $R_{=i}'$, $R_="$ is mono-olefin having a carbon skeleton different from that of R', R" is terminal alkyl having the same carbon skeleton as $R_="$, $R_{=t}'$ is terminal olefin having the same carbon skeleton as R' and $R_{=i}'$, and $R_="$ may be the same as or different from $R_=$.

DESCRIPTION OF THE PREFERRED EMBODIMENTS

As it is used in the specification and claims, the term "terminal olefin" shall mean ethylene and propylene, as well as higher molecular weight monoolefins wherein at least 50 mole percent of the olefinic molecules have a carbon-to-carbon double bond between the first and second carbon atoms in the longest continuous chain of carbon atoms in the olefin molecule.

The terminal olefin useful in the process of the present invention includes various compounds comprising, in addition to carbon and hydrogen, one or more of a variety of substituents which do not prevent the carrying out of the process of this invention. Typically of greatest interest, however, is the production of terminal olefinic hydrocarbons, i.e., those containing only hydrogen and carbon. As noted above, terminal olefin is inclusive of short chain olefins such as ethylene and propylene, although the invention typically has its greatest utility in production of longer chain terminal olefins. Such olefins are of considerable use in the production of various terminally functionalized compounds. For example, they can be oxidized and hydrolyzed to produce the corresponding alcohols, or they can be reacted with boron or aluminum hydrides to produce the corresponding organo-metallic compounds. Other uses will be evident to those skilled in the art.

The mono-olefin employed in the preparation of such terminal olefins by the aforementioned single-step embodiment of the process of this invention is an olefin having a carbon skeleton that is different (i.e., in its number of carbon atoms or the arrangement thereof) from that of the alkyl group it is to displace from the recited zirconium compound, and hence also different from that of the terminal olefin which results from such displacement. Thus, in that embodiment, the mono-olefin may be an internal or terminal olefin, e.g., ethylene, propylene, 2-butene, 4-octene, etc. In the aforementioned two-step (olefin isomerization) embodiment of the invention, on the other hand, the mono-olefin reactant employed in Step (A) is an internal olefin, i.e., a mono-olefin which is not a terminal olefin as defined hereinbefore. In other words, such mono-olefins are those susceptible of migration of a double bond from an internal position to a terminal position. Included among such internal olefins are, for example, 2-butene, 2-pentene, 2-hexene, 3-hexene, 2-methyl-3-heptene, 2-octene, 3-octene, 4-octene, 4-decene, 3-undecene, 2-methyl-3-amyl-3-hexene, β-methyl styrene, ethyl styrene, isopropyl styrene, and the like. Any of such internal or terminal olefins can be further substituted with hydrocarbyl or other groups which do not prevent the carrying out of the process of this invention, and the use of mixtures of appropriate olefins is of course also within the scope of this invention.

Particularly useful in this invention are mono-olefins containing up to about 25 carbon atoms and especially those containing up to about 20 carbon atoms, mono-olefins which are wholly hydrocarbyl (i.e., composed of hydrogen and carbon) and especially olefinic hydrocarbons of the straight-chain variety. In most embodiments, the mono-olefins employed advantageously contain at least 3 carbon atoms to keep down somewhat the reaction pressure required to maintain the vapor pressure of that olefin at the reaction temperature employed. In the two-step embodiment of the process, the invention generally has greatest utility in the isomerization of olefins containing from about 6 up to about 20 carbon atoms and especially those containing from about 10 to about 16 carbon atoms. For purposes of separating unreacted mono-olefinic reactant from terminal olefinic product in any embodiment of the invention, it is advantageous if they differ in a way that facilitates separation by the method desirably used. For example, when the separation is by distillation, it is advantageous if they differ significantly is volatility, such as, for instance, if the number of carbon atoms in that product is at least 1 (preferably at least 2) greater or smaller than the number of carbon atoms in that reactant. Accordingly, mono-olefins containing between 3 and about 9 carbon atoms are advantageously used in various embodiments of the invention such as, for example, in Step (B) of many preferred embodiments of the two-step (isomerization) process of this invention. Of course, other separation techniques such as solvent extraction, molecular sieves, etc., may be used if desired, and in such instances the two olefins will advantageously differ in ways facilitating their separation by the particular separation technique to be used.

In each of the foregoing formulae (1) and (3) of the zirconium compounds employed in this invention, the radicals represented by Cp may be the same as or different from each other and are in general any π-cyclopentadienyl radicals which are directly linked to the Zr atom in that formula and which do not prevent displacement of the recited terminal alkyl group from the compound having that formula in accordance with the process of this invention. Typical but not limiting examples of the radicals which may be represented by Cp in those formulae include a π-cyclopentadienyl radical that is unsubstituted (i.e., devoid of ring substituents other than hydrogen) and substituted π-cyclopentadienyl radicals such as a π-indenyl, π-fluorenyl, tetrahydro-π-indenyl, octahydro-π-fluorenyl, pentamethyl-π-cyclopentadienyl, pentaethyl-π-cyclopentadienyl, heptamethyl-π-indenyl, nonamethyl-π-fluorenyl or undecamethyl-tetrahydro-π-indenyl radical. Any of such radicals can be differently or further substituted (e.g., with other normal alkyl or cycloalkyl groups, with branched alkyl groups or with alkoxy or phenoxy groups) provided such substituents do not prevent displacement of the recited terminal alkyl group from the compound represented by that formula by use of a mono-olefin in accordance with the process of this invention.

Certain of such substituents may advantageously increase the solubility of the zirconium compound in an excess of the mono-olefinic reactant or in an extraneous solvent employed in the process of this invention, and a considerable amount of such substitution may be present in some cases. Where there is alkyl substitution of the ring(s) of such radicals it is typical for each alkyl substituent to contain from 1 to about 12 and even more typically from about 1 to about 4 carbon atoms and/or for the average number of carbon atoms per alkyl substituent to be not greater than about 2.

Other examples of substituents optionally present on a $\pi$-cyclopentadienyl ring in the radicals represented by Cp include various polymeric materials such as, for example, a polystyrene. In some embodiments it may be advantageous for such a polymeric material to have sufficient molecular weight that it is a solid (e.g., a polymeric resin) under the conditions of the process of this invention, thereby facilitating maintenance of the zirconium compound in a fixed position for ease of separation of a terminal olefin product of the process disclosed herein.

As aforesaid, the zirconium compounds employed in this invention also comprise a monovalent entity (designated X) that is essentially non-interfering or, in other words, which does not prevent displacement of the recited terminal alkyl group from that compound by the particular mono-olefin reactant employed. In referring to X as a monovalent entity, it is not meant that said entity must be a monovalent atom, but only that it is monovalently linked to the zirconium atom in a compound of the kind represented by formulae herein. Thus, X can be a monovalent atom such as a halogen, a more complex entity such as an alkoxy (e.g., methoxy, ethoxy or the like) or phenoxy radical, or even a much bulkier entity such as a normally solid material (e.g., a polymeric material such as a polystyrene) which may advantageously anchor the zirconium compound in a fixed position for ease of product separation as referred to hereinbefore. Preferred among such monovalent entities are the lower ($C_1$–$C_4$) alkoxy radicals and the halogens, i.e., a member of Group VII$b$ in the Periodic Table of the Elements. Chlorine and bromine are generally preferred for economic reasons, and chlorine is normally most preferred.

Also as aforesaid, the zirconium compound employed herein comprises a terminal alkyl group. As used herein, "terminal alkyl" means an alkyl group which is directly linked to the zirconium atom in that compound through a carbon atom situated on one end of the longest continuous chain or carbon atoms in that alkyl group, and is inclusive of ethyl, n-propyl, n-butyl, 1-isobutyl, n-pentyl, 1-isopentyl, 1-tert-pentyl, n-hexyl, n-octyl, n-undecyl, n-dodecyl, and variations thereof having substituents (cycloalkyl, aryl, alkoxy, phenoxy, halo or the like) which do not prevent displacement of that alkyl group from the zirconium compound in accordance with the process of this invention.

Any of the aforementioned zirconium compounds can be prepared using procedures of the kind identified in the aforecited article by Schwartz and Labinger (substituting other of the aforementioned non-interfering monovalent entities for chlorine and/or substituted $\pi$-cyclopentadienyl for unsubstituted $\pi$-cyclopentadienyl radicals, as appropriate) or by other procedures described in the art such as, for example, by reacting a zirconium salt having the formula $ZrX_4$ wherein X has the aforedescribed significance (e.g., a zirconium tetrahalide, tetra-alkoxide or the like) with an appropriate $\pi$-cyclopentadienyl sodium salt, which can be made by reacting sodium hydride with an alkyl-$\pi$-cyclopentadiene having such additional ring substituents as are desired, and converting the resulting $Cp_2ZrX_2$ compound to the corresponding mono-hydride ($Cp_2ZrXH$) and then to its corresponding alkyl derivative ($Cp_2ZrXR$), again by procedure of the kind identified in that article by Schwartz and Labinger.

Although this process may be carried out satisfactorily using zirconium compounds comprising $\pi$-indenyl or $\pi$-fluorenyl radicals, it is a preferred embodiment of the process which utilizes such a compound comprising two mono-cyclic-$\pi$-cyclopentadienyl radicals such as, for example, unsubstituted $\pi$-cyclopentadienyl or pentamethyl-$\pi$-cyclopentadienyl radicals.

In each of the reaction steps of the various embodiments of the process of this invention, the recited zirconium compound and mono-olefin reactants are subjectedto reaction conditions under which the terminal alkyl radical represented by R (or R') is displaced from that compound by the mono-olefin, meaning that the mono-olefin takes the place of that terminal alkyl radical which is liberated in the form of the terminal olefin produced by that reaction step. The particular conditions of temperature and pressure most desirably employed vary widely depending on the particular mono-olefin and terminal alkyl group involved. In general, it is desirable to use a reaction pressure somewhat below the vapor pressure of the resulting terminal olefin when that terminal olefin is more volatile than the mono-olefin employed in the process, in order to withdraw (distill) such terminal olefin during the reaction (preferably essentially as it is formed) and thereby drive the displacement reaction in the desired direction. In process embodiments in which the mono-olefin is more volatile than the resulting terminal olefin, it is preferable to use a reaction pressure at least equal to the reaction vapor pressure of that mono-olefin and drive the reaction in the desired direction by carrying it out in the presence of a substantial stoichiometric excess (generally at least about 10 percent and preferably at least about 50 percent) of the mono-olefin. The temperature employed should be high enough to drive the reaction at a suitable rate but not so high as to cause intolerable decomposition or side reactions of the desired product and/or reactants.

In general, temperatures between about 0° and about 200° C. can be employed depending on the particular reactants involved, and in most cases a temperature between about 50° and about 120° C. is preferred. Of particular advantage and great practical significance is the discovery that the production of many useful terminal olefins by this process can be carried out with attractive reaction rates at temperatues below 100° C., e.g., between about 60° and about 95° C. Although an elevated pressure is not essential, some advantage is normally achieved in employing superatmospheric pressure, particularly when the mono-olefin employed in the reaction is relatively volatile. Pressures up to about 50 atmospheres or even higher are suitable in many instances, although normally a reaction pressure between about 1 and about 20 atmospheres can be satisfactorily employed.

In most instances, the use of a reaction solvent is optional. Typically, the presence of a substantial excess of the mono-olefin reactant provides a satisfactory solvent effect but, if desired, the reaction can be carried out in a solvent for the zirconium compound reactant that does not prevent its terminal alkyl substituent from being displaced therefrom by the mono-olefin reactant. Normally, there are various solvents which can be used satisfactorily. For example, ethereal solvents such as dioxane, tetrahydropyran, tetrahydrofuran, diethylether and ethyleneglycol dimethyl ether (glyme) are generally superior solvents for such use, and tetrahydrofuran is especially preferred. Ethylether, dimethylether and anisole are other ethereal solvents which may be similarly used. Various tertiary amines (e.g., trimethylamine) and aromatic hydrocarbons (e.g., benzene, toluene, the xylenes and naphthalene) are similarly useful.

At this point it must be re-emphasized that the optimum reaction conditions are highly dependent on the particular reactants to be used. Using the guidelines provided herein, however, those skilled in the art will have little difficulty in selection reaction conditions including temperature, pressure, ratios of reactants, use of a solvent, etc., which will provide satisfactory results.

In the reaction generically represented in the single-step process embodiment of this invention, there is produced in addition to the terminal olefin product a second zirconium compound which differs from its precursor zirconium compound in that its terminal alkyl constituent (herein designated R') has the same carbon skeleton as the mono-olefin theretofore reacted with that precursor. That second zirconium compound may be used, if desired, in production of a terminally halogenated or other terminally functionalized alkane by a procedure such as that described in the aforecited article by Schwartz and Labinger or, in accordance with another embodiment of the present invention, it may be mixed with a second mono-olefin having a carbon skeleton different from that of its terminal alkyl constituent (R') and then subjected to reaction conditions under which that substituent is displaced by that second mono-olefin. This has application in the aforementioned two-step process embodiment by which a mono-olefin reacted with the first zirconium compound is isomerized to the corresponding terminal olefin after passing through an intermediate status as a terminal alkyl substituent of the reacted zirconium compound.

In view of the aforementioned prior art, it is most surprising that a terminal olefin can be liberated from such a zirconium compound by reaction with a mono-olefin, and particularly with mono-olefins containing carbon atoms more numerous than those in ethylene, which would be normally expected to be the most reactive of all olefins for such a purpose. It is additionally surprising to find that by proper control of process conditions as described hereinbefore, this reaction can be carried out in two different steps with the zirconium compound produced in the mixture employed in the first of such steps being withdrawn from that mixture and then reacted with a second mono-olefin with the resulting production of the terminal olefin isomer of the internal mono-olefin reacted in the first of those steps.

Thus, there is provided by the invention a two-step process embodiment which can be carried out, if desired, with recycle of a terminal olefin produced in one step for reuse as the mono-olefin reactant employed in the other step. Clearly, such a process embodiment has a very significant advantage in that although two terminal olefins are formed, one of them (typically the one containing fewer carbon atoms) is fully reusable in production of the other and therefore does not become a by-product of the preparation of that other (desired) terminal olefin.

Relating this further to the two-step process embodiment for isomerization of an internal mono-olefin, as described and illustrated hereinbefore, it is an advantageous mode of operation wherein (4) has the same carbon skeleton as R, and (1) which is thus formed in Step (B) is withdrawn from the mixture of (3) and (4) and then recycled for combination with and reuse in the mixture of (1) and (2) employed in step (A). Such reuse of (1) in that mode of operation results in regeneration of (4) which can then be withdrawn from the mixture of (1) and (2) employed in Step (A) and thereafter reused in Step (B), thus permitting an economically attractive essentially continuous reuse of that mono-olefin (4).

In another preferred embodiment of the two-step (isomerization) process of this invention, a terminal olefin which is produced in Step (A) and which is more volatile than the mono-olefin reactant used in Step (A) can be advantageously withdrawn from the mixture of (1) and (2) during Step (A), as aforesaid, leaving a mixture enriched in (3) which can then be conveniently used in Step (B) of the process.

Any of such process embodiments can be combined, if desired, in a continuous two-step operation in which at least a substantial proportion (preferably essentially all) of the terminal olefin formed in Step (A) is employed as the mono-olefin (4) in Step (B), at least a substantial proportion (preferably essentially all) of the zirconium compound (3) formed in Step (A) is employed in Step (B), at least a substantial proportion (preferably essentially all) of the zirconium compound (1) formed in Step (B) is recycled for reuse in Step (A), mono-olefin (2) is continuously fed to the mixture used in Step (A) and the desired terminal olefinic isomer thereof is continuously withdrawn from the mixture used in Step (B). Such an operation, in which the two reaction steps can be carried out simultaneously if desired, may be illustrated as follows:

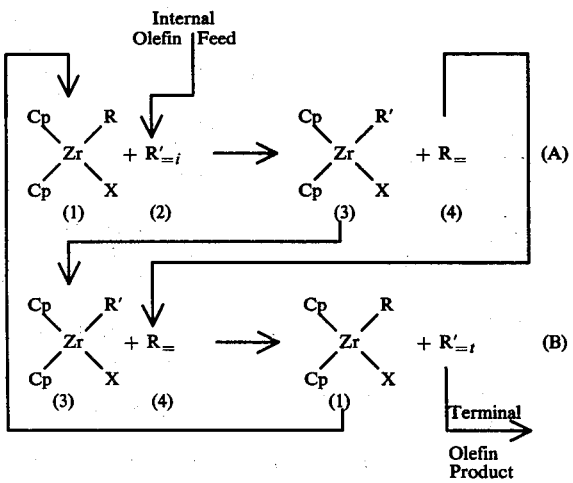

wherein Cp, X, R, R', R$_{=}$', R$_{=}$ and R$_{=}$' have their aforedescribed significance, each arrow between Steps (A) and (B) represents withdrawal of the indicated reaction product from the mixture in which it is formed and then combination of that withdrawn product with the reaction mixture employed in the other step of the process and, as described hereinbefore, the reaction conditions in the two process steps (e.g., pressure, ratios of reactants, temperature, etc.) are controlled such that they differ sufficiently that both reactions proceed at satisfactory rates.

In such a continuous operation or otherwise, any internal olefin withdrawn from either mixture can be separated by techniques known in the art from the terminal olefin produced in that mixture and recycled for further reaction. In still another mode of operation, when the mono-olefin (2) is fed to Step (A) as a component of a mixture comprising other constituents such as paraffins or the like, such other constituents may be conveniently withdrawn from the mixture used in Step (A) together with the terminal olefin formed in that step. This makes possible the use of the two-step (isomerization) process embodiment of this invention for simultaneous separation of such other constituents from the internal mono-olefin (2) to be isomerized.

The following specific examples are illustrative only and do not imply any limitations on the scope of the invention.

EXAMPLE I

A well-stirred mixture of 27.72 gms (82.4 mmoles) of the compound having the structural formula

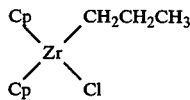

wherein Cp is an unsubstituted $\pi$-cyclopentadienyl radical (hereinafter Compound A) and 163.6 gms of C$_{12}$ olefins and paraffins containing 25.3 gms (150.8 mmoles) of mono-olefin of which 80 mole percent is internal mono-olefin in 270 ml of tetrahydrofuran (THF) is maintained at 80° C. and essentially atmospheric pressure. A slow argon purge of the reaction vessel is employed to help carry evolved propylene over to a cold trap, and the progress of the reaction is followed by VPC analysis of iodinated aliquots, furnishing the following data (based on the mmoles of Compound A originally present in the mixture):

| Reaction Time, Hours | Mole % Compound A | Mole % Compound B* |
|---|---|---|
| 6.5 | 63 | 21 |
| 9.5 | 51 | 27 |
| 21.5 | 19 | 33 |
| 33.0 | 16 | 32 |

*(same formula as Compound A except that the terminal alkyl substituent is n-dodecyl)

The THF is removed by vacuum distillation at room temperature, and 153.25 grams of unreacted C$_{12}$ olefin and paraffin is withdrawn from the mixture by distillation at 35° C. and 0.03 mm Hg. over a 12 hour interval. Analysis of the recovered material shows that 33.3 mmole of C$_{12}$ olefin had been consumed in the reaction. The residue is taken up in THF and filtered, leaving a solution which is found to contain 11.47 mmole of Compound B.

EXAMPLE II

A well-stirred mixture of 13.14 mmole of the compound having the structural formula

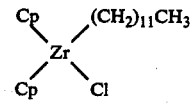

wherein Cp is an unsubstituted $\pi$-cyclopentadienyl radical (Compound B, as produced in Example I) and 200 mmole of propylene in 40 ml of THF is maintained at 80° C. and 11.4 atm. for 11 hours. VPC analysis of iodinated aliquots taken at the end of that time shows that 57 percent of the Compound B reactant has been converted to the aforedescribed Compound A. A mixture of olefin and paraffin withdrawn from the mixture by vacuum distillation at 33° C. and 0.02 mm is found to contain 12 percent n-dodecane and 65 percent n-dodecene of which over 90 percent is terminal n-dodecene.

EXAMPLE III

The reactions of Examples I and II are carried out concurrently, continuously and in dynamic equilibria with propylene and Compound B being withdrawn from the Example I reaction mixture and then combined in the proper proportions with the Example II reaction mixture, and with internal n-dodecene withdrawn from the Example II reaction mixture being recycled to the Example I reaction mixture. The mixture of C$_{12}$ olefin and paraffin is continuously fed to the Example I reaction mixture, and terminal n-dodecene is continuously recovered from the Example II reaction mixture.

EXAMPLE IV

A well-stirred mixture of 15.76 mmole of Compound A and 31.81 gms of C$_{12}$ olefins and paraffins containing 22.5 mmoles of mono-olefin in 60 ml of benzene is maintained at 50° C. for 2 hours, 80° C. for a third hour, 85° C. for a fourth hour and then 95° C. for a fifth hour, all at essentially atmospheric pressure. VPC analysis of a brominated sample taken at the end of that time shows that 32 percent of the Compound A reactant has been converted to the aforedescribed Compound B.

EXAMPLE V

A well-stirred mixture of 7.8 mmoles of the aforedescribed Compound B and 4.6 gms of propylene in 27 ml of benzene is maintained at 80° C. and 7.8 atm. for 1.5 hours and then at 90° C. and 8.5 atm. for an additional 1.5 hours. VPC analysis of a brominated aliquot taken at that time indicates the presence of 3.6 mmoles of the aforedescribed Compound A. After removal of the benzene by vacuum distillation at room temperature, there is withdrawn from the mixture by distillation at 30° C. and 0.03 mm over a period of several hours a mixture of olefin and paraffin which is found to contain 19 percent n-dodecane and 44 percent n-dodecene of which 94 percent is terminal n-dodecene.

EXAMPLE VI

A well-stirred mixture of 14.4 mmole of the compound having the structural formula

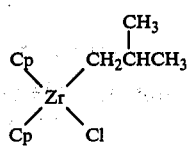

wherein Cp is an unsubstituted π-cyclopentadienyl radical (hereinafter Compound C) and 28.53 gms of $C_{12}$ olefins and paraffins containing 20.2 mmoles of mono-olefins in 60 ml of benzene is maintained at 80° C. and essentially atmospheric pressure for 5 hours. VPC analysis of a brominated sample taken at the end of that time shows that 41 percent of the Compound C reactant has been converted to the aforedescribed Compound B.

The embodiments of this invention in which a particular property or privilege is claimed are described as follows:

1. A process which comprises bringing together (1) a compound having the formula

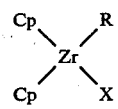

wherein each Cp is a π-cyclopentadienyl radical, R is terminal alkyl and X is an essentially non-interfering monovalent entity and (2) mono-olefin having a carbon skeleton different from that of R under reaction conditions to displace R from (1) with (2).

2. The process of claim 1 which further comprises recovering terminal olefin having the same carbon skeleton as R.

3. The process of claim 1 which further comprises recovering a compound having the formula

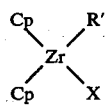

wherein Cp and X have their aforedescribed significance and R' is terminal alkyl having the same carbon skeleton as (2).

4. The process of claim 1 wherein the number of carbon atoms in (2) is different from that in R.

5. The process of claim 1 wherein (2) is an internal mono-olefin.

6. The process of claim 1 wherein X is halogen, each of R and (2) is composed of hydrogen and up to about 25 carbon atoms, and at least one of R and (2) comprises a straight chain or at least 4 carbon atoms.

7. The process of claim 6 wherein each of R and (2) is straight-chain and contains up to about 20 carbon atoms.

8. The process of claim 6 wherein each of R and (2) contains at least 3 carbon atoms.

9. The process of claim 6 carried out in a solvent for (1) that does not prevent R from being displaced from (1) by (2) under said conditions.

10. The process of claim 6 wherein said halogen is chloride and each Cp is an unsubstituted π-cyclopentadienyl radical.

11. The process of claim 10 wherein R contains from about 6 to about 20 carbon atoms, (2) contains from 3 to about 9 carbon atoms, the number of carbon atoms in R is at least 1 greater than the number of carbon atoms in (2) and said process is carried out at a temperature between about 50° and about 120° C. and in the presence of a stoichiometric excess of (2) of at least about 10 percent.

12. The process of claim 11 wherein (2) is propylene.

13. The process of claim 10 wherein R contains from 3 to about 9 carbon atoms, (2) is mono-olefin containing from about 6 to about 20 carbon atoms, the number of carbon atoms in (2) is at least 1 greater than the number of carbon atoms in R and said process is carried out with simultaneous removal of a terminal olefin having the same carbon skeleton as R from the mixture.

14. The process of claim 13 wherein (2) is internal mono-olefin.

15. The process of claim 14 wherein R is propyl.

16. A process for isomerizing an internal olefin to a terminal olefin, which process comprises the following steps:

(A) subjecting (1) a compound having the formula

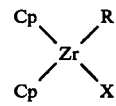

wherein each Cp is a π-cyclopentadienyl radical, R is terminal alkyl and X is an essentially non-interfering monovalent entity and (2) internal mono-olefin having a carbon skeleton different from that of R to reaction conditions under which R is displaced from (1) by (2) forming (3) a compound having the formula

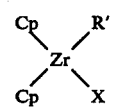

wherein Cp and X have their aforedescribed significance and R' is terminal alkyl having the same carbon skeleton as (2) and (B) subjecting (3) formed by Step (A) and (4) mono-olefin having a carbon skeleton different from that of R' to reaction conditions under which R' is displaced from (3) by (4) forming terminal olefin having the same carbon skeleton as (2).

17. The process of claim 16 wherein each of R, (2) and (4) is composed of hydrogen and up to about 25 carbon atoms, the number of carbon atoms in (2) is different from that in (4), and X is halogen.

18. The process of claim 17 wherein each of R, (2) and (4) contains at least 3 carbon atoms.

19. The process of claim 18 wherein said halogen is chlorine and each Cp is an unsubstituted π-cyclopentadienyl radical.

20. The process of claim 19 wherein R contains up to about 9 carbon atoms, (2) contains from about 6 to about 20 carbon atoms, the number of carbon atoms in (2) is at least 1 greater than the number of carbon atoms in R, and terminal olefin formed in Step (A) and having the same carbon skeleton as R is withdrawn during Step (A).

21. The process of claim 20 wherein (4) is propylene.

22. The process of claim 16 wherein (4) has the same carbon skeleton as R, and (1) formed in Step (B) is withdrawn and then combined with (1) and (2) employed in Step (A).

23. The process of claim 22 wherein each of (2) and (4) is composed of hydrogen and up to about 25 carbon atoms, and the number of carbon atoms in (2) is different from that in (4).

24. The process of claim 23 wherein X is halogen and each Cp is an unsubstituted π-cyclopentadienyl radical.

25. The process of claim 24 wherein R contains between 3 and about 9 carbon atoms, (2) contains between about 6 and about 20 carbon atoms, and the number of carbon atoms in (2) is at least 1 greater than the number of carbon atoms in R.

26. The process of claim 25 wherein (4) formed in Step (A) is withdrawn during Step (A) and then combined with (3) and (4) employed in Step (B).

27. The process of claim 26 wherein (2) contains from about 10 to about 16 carbon atoms, the halogen is chlorine and (4) is propylene.

* * * * *